United States Patent [19]
Zeligs

[11] Patent Number: 6,093,706
[45] Date of Patent: Jul. 25, 2000

[54] COMBINED DEHYDROEPIANDROSTERONE AND RETINOID THERAPY FOR EPITHELIAL DISORDERS

[75] Inventor: Michael A. Zeligs, Long Beach, Calif.

[73] Assignee: BioResponse, L.L.C., Boulder, Colo.

[21] Appl. No.: 07/845,560

[22] Filed: Mar. 4, 1992

[51] Int. Cl.$^7$ .................................................. A61K 31/56
[52] U.S. Cl. ............................................................ 514/171
[58] Field of Search .............................................. 514/171

[56] References Cited

U.S. PATENT DOCUMENTS

| | | | |
|---|---|---|---|
| 4,496,556 | 1/1985 | Orentreich | 514/178 |
| 4,542,129 | 9/1985 | Orentreich | 514/178 |
| 4,628,052 | 12/1986 | Peat | 514/171 |
| 4,889,847 | 12/1989 | Kligman et al. | 514/171 |

OTHER PUBLICATIONS

William Regelson, M.D., Cancer Investigation, Vitamin A, Dehydroepiandrosterone (DHEA) and 5' Nucleotidase: Regulatory Factors in Tumor Growth, 1985, pp. 407–409.

Feingold, "A Dermatological Viewpoint of the Permeability Barrier," *Cosmetics & Toiletries, 107*, 41–42 (1992).

Li et al., "Age dependent lipid and protein changes in individual bovine lenses," *Current Eye Research, 6,* 599–605 (1987).

Regelson et al., "Dehydroepiandrosterone (DHEA): The Precursor Steroid: Introductory Remarks," *Dehydroepiandrosterone (DHEA)*, 1–6 (1990).

Regelson et al., "DHEA: Some Thoughts as to Its Biologic and Clinical Action," *Dehydroepiandrosterone (DHEA),* 405–445 (1990).

*Primary Examiner*—Marianne M. Cintins

[57] ABSTRACT

The present invention relates to compositions and methods for the treatment of oxidative epithelial damage, for inadequate surfactant production in lung disorders, and for disorders of the urinary bladder epithelium. The compositions of the present invention comprise dehydroepiandrosterone and vitamin A derivatives.

57 Claims, No Drawings

COMBINED DEHYDROEPIANDROSTERONE AND RETINOID THERAPY FOR EPITHELIAL DISORDERS

FIELD OF THE INVENTION

The present invention relates to methods of using dehydroepiandrosterone (DHEA) and its derivatives in combination with vitamin A derivatives (retinoids) for the treatment and prevention of disorders of epithelial tissues.

BACKGROUND OF THE INVENTION

With aging, in both men and women, skin becomes thin, transparent, dry, and prone to uncontrolled growth of its superficial or epidermal layer. Sun exposure produces "photo-aging," which accelerates these changes and stimulates the development of premalignant, raised, roughened areas (actinic keratoses), and malignant tumors (squamous and basal cell carcinomas).

In aging skin, at the microscopic level, the outermost layer of cells, or "stratum corneum," shows diminished cellular cohesion. Furthermore, dry or cornified cells are shed more rapidly than in younger skin. In the deeper granular layer, the predominant cell type, called the keratinocyte, is known to have fewer intracellular keratohyalin granules and fewer subcellular organelles in older skin compared to younger skin.

The lipid-based "epidermal water barrier," which emanates from the granular layer, has been shown to have reduced complex lipid and ceramide content in aged skin when compared to younger skin. The characteristic subcellular organelle of the granular-layer keratinocyte is the "lamellar body" or "keratinosome," which is composed of phospholipids, ceramides, and free sterols. The lamellar bodies migrate to the periphery of the granular cell, where they fuse with the plasma membrane and expel their contents into the intercellular space. Once in the intercellular space, ceramides organize to form the intercellular cement, holding together the more superficial corneal cells and constituting the lipid barrier of the epidermis.

The precursors for biosynthesis of ceramides and specialized lipids include essential fatty acids and the action of subcellular organelles, called "microbodies" or "peroxisomes." Peroxisomes are enzyme-rich and are known to participate in the metabolism of long-chain fatty acids derived from the essential fatty acids.

Both exposure to ultraviolet light and aging are associated with diminished peroxisome numbers and enzymatic activity.

Basal cells form the deepest epidermal cell layer. With aging, they become shorter and less adherent to the dermal layer below. Their nuclei become irregularly shaped, supplying further evidence of disordered growth and differentiation of older, as compared to younger, skin.

Chronic sun exposure predominantly alters the dermis, where elastic fibers thicken, degrade, and degenerate in amorphous masses. Collagen is damaged due to proteolytic enzymes associated with ultraviolet-light-induced inflammation. As a result, wrinkles become deeper and permanent. Also within the dermis, sebaceous glands become larger and contain more cells, even though their production of sebum is less.

Therapy for skin-aging and photo-damage has been advocated to reduce occurrence of epidermal cancer with advancing age. Such therapies have included the use of sun-blocking chemicals, such as para-aminobenzoic acid and methoxy-cinnamate.

Most recently, topical therapy with active vitamin A derivatives, especially retinoic acid, have been shown to specifically stimulate tissue repair in the dermal layer and proliferation and thickening of the more superficial epidermal layers. Retinoid therapy results in a reduction of fine wrinkles, promotion of new collagen synthesis, and reduction of the occurrence of sun-induced basal cell carcinomas. However, retinoic acid therapy often causes dryness, redness, burning, peeling, and increased sun sensitivity of the skin. These side effects make retinoic acid therapy unacceptable to many individuals.

Microscopic study of retinoic acid-treated skin reveals altered keratin protein production, reduced cell-to-cell cohesion, changes in the composition of the lipid barrier of the granular layer, and cellular disorganization of the superficial stratum corneum. An increase in trans-epidermal water loss is seen with retinoid therapy which is similar to that observed in atopic dermatitis and congenital deficiency of the lipid barrier in ichthyosis.

Systemic therapy using oral retinoic acid has proved useful in preventing precancerous changes in the oral mucosa of the elderly ("leukoplakia") and in preventing the development of new tumors in individuals who have had previous squamous cell carcinomas of the head and neck. However, such systemic therapy with retinoids results in similar, or more severe, toxic reactions than those observed with topical use, including pseudo tumor cerebri, hepatitis, dry eye syndrome, hyperostosis, and hyperlipidemia.

A need exists for improved therapy to protect the skin from ultraviolet-light-associated damage and to reduce the toxicity of current retinoid therapy for various epithelial disorders. Preferably, such treatments would stimulate the natural biosynthesis of the epidermal lipid barrier in skin that is lost with aging and diminished as a result of retinoid use.

SUMMARY OF THE INVENTION

The present invention relates to compositions and methods for the treatment of oxidative epithelial damage, inadequate surfactant production in lung disorders, and disorders of the urinary bladder epithelium. The compositions of the present invention comprise dehydroepiandrosterone (DHEA) and pharmacologically active vitamin A derivatives.

More specifically, the DHEA suitable for use in the present invention is selected from the group consisting of the free alcohol of DHEA, DHEA-S, DHEA derivatives which retain the pharmacologically activity of DHEA, and mixtures thereof, and the vitamin A derivatives are selected from the group consisting of retinoic acid, 13-cis-retinoic acid, N-(4-hydroxyphenyl)retinamide, all-trans-retinoic acid, retinal palmitate, β-carotene, other precursors and derivatives of retinoic acid, vitamin A and vitamin A derivatives, and mixtures thereof.

The DHEA/vitamin A derivative compositions may be formulated for oral, intranasal, topical, intravenous or sublingual administration.

DETAILED DESCRIPTION

The present invention provides a method for combining dehydroepiandrosterone (DHEA) with retinoids to reverse tissue changes due to aging and prevent changes due to ultraviolet light exposure.

During the aging process in most mammals, one of the most dramatic hormonal changes which occurs in both males and females is the progressive fall in DHEA. DHEA and its sulfated derivative, DHEA-S, comprise the most abundant steroid, released into the circulation by the adrenal cortex. However, starting in the third decade of life, daily secretion of the hormone begins a continuous decline, and by the seventh decade of life, a 90% reduction in DHEA blood levels is commonly observed.

Although the full range of biological activity of DHEA has not been established, it has been shown to play a role in a number of cellular activities in various tissues, such as in sebaceous gland activity in skin; in nervous tissue, as in the treatment of central nervous system degeneration, especially in Alzheimer's Disease; in treatment of diabetes; in treatment of arthritis; in promoting cervical ripening in pregnancy; in anti-carcinogenic activity; in anti-atherosclerotic activity; and in various effects on metabolism in animals, especially a proliferative effect on subcellular peroxisomes.

The composition of the present invention combines the activity of DHEA and retinoids, which combination reduces side effects and toxicity which result from the use of either DHEA or retinoids alone. The side effects of increased sebum production and associated acne, caused by DHEA's stimulation of sebaceous gland tissue, are reduced by the drying effect of retinoids, which reduce the production and release of sebaceous oil. DHEA, likewise, ameliorates the excessive skin dryness, redness, and increased photosensitivity induced by retinoids, by improving the quantity and quality of the ceramide-based lipids produced by the granular keratinocytes. The combinations of DHEA and retinoid may be delivered or administered as a single component, for example, in a single cream, or the combination may be administered separately, for example, a cream with one of the components may be administered, followed by administration of the second component.

The combinations described herein can be used topically or systemically to reduce the changes associated with intrinsic and photo-aging of skin. The combination also has an anti-proliferative, anti-carcinogenic, and differentiation-enhancing effects on other epithelial tissues.

The present invention provides a method for using DHEA and its derivatives and analogues, in combination with retinoids, to restore production of specialized lipid synthesis by keratinocytes in skin and other ectodermally-derived tissue. Specific examples of responsive non-skin keratinocytes include keratinocyte-like cell populations found in the pineal gland and the thymus.

In the present invention, DHEA is used as an agent to stimulate peroxisomes and to prevent or reverse the reduction in peroxisomal activity due to aging-related decreases in DHEA tissue levels. Without being bound by scientific theory, DHEA therapy is thought to stimulate new peroxisome formation to compensate for ultraviolet-light-induced peroxisomal inactivation. An increased peroxisome population provides for increased synthesis of the sphingolipid precursors of ceramides. In addition, stimulated peroxisomal metabolism increases resistance to oxidative stress by increasing the turnover of membrane phospholipids which have been damaged by ultraviolet-light-triggered peroxidation.

DHEA, of the present invention, acts as an agent to stimulate the peroxisomal-based biosynthesis of complex lipids, especially the sphingolipid-derived ceramides. DHEA therapy specifically stimulates keratinocytes and other hormonally-responsive epithelial cells to produce increased amounts of these and related membrane-active, structural lipids. With aging and various abnormal skin conditions, such as atopic dermatitis, psoriasis, and congenital ichthyosis, there is a reduction in epidermal ceramide content associated with scaly and dry skin. The loss of these lipids results in a deficient lipid barrier, permitting increased penetration of environmental agents into the skin and diminished repair of ultraviolet-light-induced damage.

Retinoid therapy results in the proliferative response of dermal and epidermal cell types, which partially reduces photo-aging changes. The toxic effects of retinoids are related to a further reduction in age-related deficiencies in the lipid barrier. Thus, retinoid therapy induces reversal of existing premalignant skin changes but, when combined with ongoing ultraviolet exposure, reduces resistance to oxidative damage, and can serve as a tumor promoter. DHEA counteracts these unwanted actions of retinoids.

The various forms of DHEA useful in the present invention are pharmacologically active DHEA; dehydroepiandrosterone-sulfate (DHEA-S); the free alcohol of DHEA; derivatives of DHEA, such as DHEA 3-acetate (3-hydroxy-5-androsten-17-one-acetate), DHEA-3-glucuronide (3-hydroxy-5-androsten-17-one-3-glucuronide), DHEA-hemisuccinate, DHEA-valerate, DHEA-enanthate, DHEA-fatty acid derivatives, 16-fluorinated, 16-brominated DHEA, and DHEA-salts; and other such DHEA compounds which retain the biological function and activity of DHEA.

Also useful for use in the present invention are metabolic precursors of DHEA, such as pregnenolone, and active metabolites, such as $\beta$-etiocholanolone. Other steroid hormones with weak peroxisome-inducing activity but lacking convertability to androgens, such as progesterone, are also useful when avoidance of hair follicle stimulation is necessary to minimize androgenic alopecia.

The various forms of vitamin A for use in the present invention include pharmacologically-active retinal and retinol, but especially retinoic acid (tretinoin). In addition, the highly-active synthetic vitamin A derivatives, such as 13-cis-retinoic acid (iso-tretinoin), all-trans-retinoic acid, N-(4-hydroxyphenyl)retinamide, 4-HPR(fennetinide), and other synthetic vitamin-A derivatives can also be employed, but at lower doses than the naturally-occurring vitamin A derivatives. For cosmetic applications, the less-active, naturally-occurring vitamin A derivatives, such as retinal palmitate and precursor $\beta$-carotene, may be used.

Treatments with Retinoid-DHEA Combinations
Topical Administration

The retinoid-DHEA combination may, if desired, be administered in appropriate pharmacologically acceptable carriers in such forms as creams, lotions, lipsticks, and dispersible powders.

In such treatments, DHEA and retinoids are solubilized in a suitable carrier, such as cetyl alcohol, glyceryl stearate, polyethylene glycol-100 stearate, sorbitol, water, or combinations thereof. To this basic carrier formulation are added ethylene-diaminetetraacetic acid (EDTA) and vitamin E alcohol as a preservative and an anti-oxidant, respectively, to form a cream base carrier. EDTA is added at a concentration of about 0.05% to about 0.1%. and vitamin E alcohol is added at a concentration of about 0.05% to about 0.1%. The term % as used herein is % weight by volume, unless otherwise stated.

A combined DHEA-retinoid-containing cream (0.75% DHEA, 0.075% retinoid) for topical treatment is prepared by forming an oil-in-water emulsion as follows: The water phase is prepared by mixing 50 mg of EDTA and 5 cc of propylene glycol in 85 cc of water, and heating to 65° C. for 5 min. The oil phase is then formed by combining 10 cc of cetyl alcohol and 4 cc of 21 stearyl ether, supplied under the name of Brij 721 by Sigma Chemical Co., St. Louis, Mo., Catalog No. P6153, and heating to 60° C. 750 mg of crystalline DHEA alcohol and 7.5 mg of retinoic acid is added to the heated oil phase, with constant mixing, until the DHEA and retinoic acid are dissolved. The water phase is slowly added to the oil phase, with constant mixing. The resulting emulsion is allowed to cool, and 0.1 cc of vitamin E alcohol is added to the cooled mixture. The concentrations can be varied from about 0.001% to about 0.2% for the retinoid, and about 0.05% to about 1.0% for the DHEA (w/v). Preferably, the retinoic-acid concentration is about 1%, and the DHEA concentration is about 0.75%. Application of the mixture is preferably performed at night, prior to sleep, to avoid ultraviolet light when first applied.

The treatment of oxidative epithelial damage of a mammal can be achieved by topical application of DHEA and retinoids in a cream base carrier, as described above. Oxidative epithelial damage is defined, in the present invention, to include the effects of aging on the skin as well as chronic conditions, such as atopic dermatitis, psoriasis, vernal conjunctivitis, congenital ichthyosis, scaly and dry skin, certain dry eye conditions, blepharitis, ultraviolet-induced skin damage, damage caused by chemical peel procedures, superficial burns, chronic papilloma herpes viral infection, and squamous cell carcinoma.

Topical treatment of oxidative epithelial damage can be achieved by using concentrations of DHEA and the retinoid which are at the lower of the range described above and which have been added to a cosmetic base for daytime use. The lower concentrations reduce any irritation to the skin that may result from sun exposure. In such mixtures, the retinoid concentration is about 0.001% to about 0.01%, and the DHEA concentration is about 0.05% to about 0.25%. Preferably, the retinoid concentration is about 0.01%, and the DHEA concentration is preferably about 0.1%. In this embodiment of the present invention, the cream base carrier also comprises ultraviolet-light blocking agents such as zinc oxide, para-aminobenzoic acid, or methyl-cinnamate; vitamin D; and additional lipids such as ceramides. In such mixtures, the ultraviolet-light blocking agents are at a concentration of about 2% to about 7% (octyl methoxy cinnamate) or about 1.5% to about 2.5% (titanium dioxide); the vitamin D is added at a concentration of about 0.001% to about 0.005% (1a-hydroxy vitamin $D_3$ or $1,25(OH_2)D_3$); and the additional lipids are added at a concentration of about 1% to about 10%. This cosmetic preparation is preferably used by post-menopausal women and is applied to skin prior to sun exposure.

When delivered topically for promotion of the epithelial lipid barrier, DHEA, its related metabolites, and brominated derivatives can all be used in varying concentrations and combinations, either alone or in combination with other steroids such as progesterone and estrogen, which promote ceramide and other specialized lipid biosynthesis. DHEA alcohol, or its metabolite, β-etiocholanolone, is preferably combined with a retinoid, such as tretinoin at a concentration of about 0.1%, and is suitable for use in post-menopausal women. Lower concentrations of DHEA (about 0.1%) are preferably used in combination with lower-concentration retinoids (tretinoin 0.025%), in younger women and in men of all ages, where the natural lipid barrier has been partially maintained and less androgenic activity is desired. The further addition of 5-alpha reductase inhibitors (progesterone, spirono-lactone, and 4-azasteroids [Proscar, Merck]) in concentrations of about 1% to about 5% is preferred to protect against the side effect of androgenic alopecia where such side effects are to be avoided.

When delivered topically to treat intrinsic and photo-aging of the skin, the combinations of DHEA and retinoids described herein, may also be use in further combination with other vitamins (E, D, and C); anti-oxidant peptides such as glutathione, ubiquinone, phospholipids (e.g., phosphatidylcholine and phosphatidylserine); and sphingolipids, especially ceramides. Suitable concentrations for use in the present invention are about 0.1% to about 1% of vitamin E; about 0.001% to about 0.005% of vitamin D (1α-hydroxy vitamin $D_3$ or $1,25(OH_2)D_3$); about 0.5% to about 1% of vitamin C; about 0.01% to about 0.05% anti-oxidant peptides, such as glutathione; about 0.002% to about 0.01% ubiquinone; about 1% to about 10% of phospholipids; and about 1% to about 10% of sphingolipids where such additions may be desirable.

Combinations of DHEA and retinoids can also be used with synergistically-active macrophage stimulators, such as glucans and ace-mananas; or immunomodulators, such as interferons, interferon antagonists, and interleukins; colony-stimulating and growth-stimulating factors, such as transforming growth factor beta (T-GFβ) and epidermal growth factor (EGF); or other hormones such as melatonin. For use in the present invention, glucans are used at a concentration of about 0.01% to about 0.05%; ace-mananas are used at a concentration of about 0.1% to about 0.5%; interferons are used at a concentration of about 0.01% to about 0.2%; interferon antagonists are used at a concentration of about 0.01% to about 0.2%; interleukins are used at a concentration of about 0.01% to about 0.2%; colony-stimulating factors are used at a concentration of about 0.01% to about 0.2%; growth factors (T-GFβ and EGF) are used at a concentration of about 0.01% to about 0.02%; and hormones, such as melatonin, are used at a concentration of about 0.1% to about 0.5%, where such combinations may be desirable.

The above described treatments with DHEA and retinoids alone or in combination with the other described additives will be most appropriate for oxidative damage to epithelial surfaces, which occurs in association with aging-related reductions in circulating DHEA. However, such therapy is also appropriate as a preventative therapy for chronic dermatitis in younger individuals with familial disorders of the epidermal lipid barrier. These disorders include atopic dermatitis, vernal conjunctivitis, psoriasis, and the ichthyoses. Such therapy is additionally appropriate in treating certain acquired disorders of epithelial tissue in all ages, especially chronic viral infection with the Human Papilloma Virus (HPV) and in reducing hypertrophic scar formation following burns, dermabrasion, and chemical peel procedures.

Systemic Administration

The compositions of the present invention may be administered by systemic administration in the form of parenteral, sublingual, transdermal, intranasal, or oral delivery. DHEA and retinoids, as described above, can be incorporated into nanospheres, microspheres, or liposomes for injection, and can be incorporated into cyclodextrins for sublingual and aerosol delivery. All such methods are well known to those skilled in the art.

The retinoid-DHEA combination may, if desired, also be administered in appropriate pharmacologically acceptable carriers in the form of tablets, granules, capsules, syrups and elixirs. The tablets may contain one or more compounds, in addition to the retinoid-DHEA combination, by admixing with conventional pharmacologically acceptable excipient, such as inert diluents (for example calcium carbonate, sodium carbonate, lactose, sorbitol and talc) granulating and disintegrating agents (such as starch and alginic acid) binding agents (such as sorbitol microcrystalline cellulose, gelatin and acacia) and lubricating agents (such as magnesium stearate, stearic acid and talc). The tablets may be uncoated or coated by known techniques to delay disintegration and adsorption in the gastrointestinal tract or incorporate cyclodextrans to provide a sustained action over a longer period of time.

For oral administration, the DHEA and retinoids are formulated in capsules or in sustained-release tablets. For parenteral administration, the DHEA and retinoid are solubilized in about 5% serum albumin solution with added (1:1 vol:vol) dextran (such as that supplied by Sigma Chemical Co., St Louis Mo., Cat No. D4133). For sublingual administration, the DHEA and retinoids are formulated by solubilizing in a solution of hydroxypropyl-δ-cyclodextrin, then freeze-drying and compressing into tablets. For intranasal administration, the DHEA and retinoids are formulated as for sublingual administration and resuspended in 0.9% saline or a suitable carrier for metered aerosol delivery.

For oral use, the composition of the present invention the dosage rate comprises administering DHEA from about 0.09 g to about 1 g of DHEA per day, with a retinoid of from about 0.025 to 0.2 g of retinoid per day. The treatment is conducted by administering DHEA about 3 times a day and the retinoid, about once a day. The treatment is continued for about four weeks and then adjusted to the minimally-effective dose. In one embodiment of the present invention, the retinoid, for oral use, is isotretinoin (13-cis-retinoic acid).

Treatment of a mammal by systemic administration with the compositions of the present invention is desirable to prevent the recurrence of squamous cell carcinomas in elderly individuals, or, in prematurely-born infants, to stimulate differentiation and increased surfactant production by the alveolar epithelium of the lungs. In this use, the agents specifically stimulate Type-Two alveolar cells, to produce and secrete increased amounts of surfactant. Such treatments supplement the therapy of surfactant-deficiency states, seen in chronic obstructive pulmonary disease in the elderly and in hyaline membrane disease of premature newborns. The compositions of the present invention are also useful for the systemic treatment of proliferative, aging-associated disorders of oral epithelium (leukoplakia) or urinary bladder epithelium (metaplasia), including secondary prevention of transitional cell carcinoma of the bladder.

EXAMPLE 1

Use of DHEA-Retinoid Combinations to Stimulate Differentiation and Increased Ceramide Production in Cultured Human Keratinocytes Submerged culture of normal human keratinocytes is an established experimental system for the study of the control of differentiation and growth of skin cells. Data on pharmacologic and hormonal control in this system have been found to be directly applicable to cell behavior in intact human squamous epithelium.

The following experiments utilize keratinocyte culture in conjunction with high-performance thin-layer chromatography (HPTLC), to establish the action of DHEA and synergistic combinations of DHEA and retinoids on ceramide production by keratinocytes.

Human epidermal cell cultures (HEK) were established at Clonetics Corporation, San Diego, Calif., according to established procedures. Proliferating cells, from cell line NHEK-346, were subcultured at a density of $2.5\times10^{-3}/cm^2$ in flat culture flasks, in steroid-free, 0.03 mM calcium, keratinocyte growth medium (KGM) supplied by Clonetics Corp. of San Diego. The cells were incubated at 37° C. in an humidified atmosphere of 5% $CO_2$ in air.

At the start of the experiment, equal aliquots of cells were transferred to eight new flasks containing fresh KGM with a higher calcium concentration (0.15 mM), to permit ongoing differentiation. A test medium was added to each of the flasks. The test media were as follows:

1. KGM only (Control)
2. KGM+0.004% dimethylsulfoxide (DMSO) (diluent control)
3. KGM+0.002% DMSO+0.1 μM DHEA
4. KGM+0.002% DMSO+10 μM DHEA
5. KGM+0.004% DMSO+0.1 μM Retinoic Acid (RA)
6. KGM+0.002% DMSO+10 μM RA
7. KGM+0.004% DMSO+0.1 μM RA+10 μM DHEA
8. KGM+0.004% DMSO+10 μM RA+0.1 μM DHEA The cells were harvested after an additional 72 hours incubation, counted, and observed microscopically.

Aliquots of equal numbers of viable cells from each of the eight flasks were then separately subjected to lipid extraction as follows: 100 μl of cell suspension was added to 2 ml of ethanol:diethyl ether (3:1 vol:vol), sonicated, and filtered through 0.22-micron hydrophobic microbore filters supplied by Alltex of Nevada City, Calif. The samples were dried under a stream of nitrogen, redissolved in 60 μl chloroform:methanol (2:1 vol:vol), and frozen under nitrogen at −70° C. until processed further.

Ceramide analysis was performed in a two-step procedure on HPTLC plates (silica 60, 10×20 cm plates supplied by Merck of West Point, Pa. Five μl of the samples were applied onto the plates. The plates were developed to 5.5 cm in solvent system I (methanol:chloroform:water, 20:95:1, by volume) and dried in cool air. The plates were then developed to 9.0 cm in solvent system II (petroleum ether:diethylether:acetic acid, 70:30:10, by volume). Subsequently, they were dried under a stream of warm air.

Lipid spots were visualized by degradative charring. After chromatography, the plates were sprayed with 10% Cu-II-acetate (w/v) in 8% (w/v) o-phosphoric acid and charred for 64 min. at 155° C. in a gaschromatograph oven. Quantification of lipids was by comparison with commercially available lipid standards (supplied by Sigma Chemical Co.) were run on the same plate every time: cholesterol-3-sulfate (Catalog No. C9523), cerebroside type II (Catalog No. C1516), ceramide type III (Catalog No. C2137), ceramide type IV (Catalog No. C2512), cholesterol (Catalog No. C8523), triolein (Catalog No. T4141), cholesteryl oleate (Catalog No. C9253), palmitic acid (P-9767), squalene (S-3626), and n-pentacosan (Catalog No. P7260). Lipid standard mixtures containing 100 ng to 2 μg of each lipid were applied to each plate.

The comparison of the lipids extracted from the treated cells to the lipid standards demonstrated increases in the quantity and variety of ceramide lipids from keratinocytes stimulated by DHEA. Ceramide production was not stimulated by retinoic acid, but the combinations of DHEA and retinoic acid produced a unique pattern of ceramide production, as well as affecting the quantities of other classes of lipids produced.

EXAMPLE 2

Use of the Hairless Mouse to Demonstrate the Topical and Photo-Protective Action of DHEA-Retinoid Combinations The Skh hairless mouse has been used as a model to study the photo-aging effects of chronic, low-dose ultraviolet (UV) radiation on the skin. There are dramatic changes in the appearance of the skin surface, described as wrinkling and sagging. In addition, tumors develop, consisting of papillomas and carcinomas. Histologically, there are a number of alterations in the epidermis and dermis which are similar to those observed in sun-exposed human skin. For these reasons, the hairless mouse model was used to demonstrate the specific protective effect of DHEA-retinoid combinations in the following protocol.

Female, albino, hairless Skh:HR-1 mice were obtained from Charles Rivers Laboratories. They were 12 weeks old at the start of trials. The mice were housed individually in special radiation cages and had free access to food and water.

Animals were irradiated for 15 min., three times a week for 15 weeks, with a bank of four Westinghouse FS20 sunlamps, placed 45 cm above their backs. Within the UV spectrum, about half the radiation was in the UV-B range (280–320 nm), while the remainder was in the UV-A range (320–400 nm). Less than 1% of the emission was below 280 nm (UV-C range). Flux was measured with an IL 700 A Radiometer (International Light, Newburyport, Mass). The daily doses of UV-B and UV-A were 0.09 $J/cm^2$ and 0.07 $J/cm^2$, respectively. Animals were randomly divided into one of five groups of seven mice each and treated with:

1. 100 μl acetone (control)
2. 100 μl acetone+10 μg trans-retinoic acid (RA)
3. 100 μl acetone+10 μg DHEA
4. 100 μl acetone+10 μg DHEA+1 μg RA
5. 100 μl acetone+1 μg DHEA+10 μg RA.

Twenty-four hours prior to each cycle of irradiation, each group received the above treatment, distributed evenly over the skin of the back.

Weekly observations were made on all animals. These observations included uniform scoring as to wrinkle scale for the quantification of tumors and skin appearance. The grading scale is presented in Table I.

TABLE I

| Grade | Description of Grading Scales for Visible Skin Changes |
| --- | --- |
| | Description of Skin |
| Skin wrinkling | |
| 0 | Numerous fine striations covering back and sides of body. Fine striations run length of body (head-to-tail direction). |
| 0.5 | Loss of fine striations on back along spine. Numerous fine striations along sides run length of body (head-to-tail direction). |
| 1.0 | No fine striations on back and along sides. Skin is smooth. |
| 1.5* | No fine striations on back and along sides. Some shallow permanent wrinkles across back (perpendicular to head-to-tail direction). |
| 2.0* | No fine striations on back and along sides. Several shallow to moderately deep permanent wrinkles across back (perpendicular to head-to-tail direction). |
| 2.5* | No fine striations on back and along sides. Numerous moderately deep to deep permanent wrinkles across back (perpendicular to head-to-tail direction). |
| 3.0* | No fine striations on back and along sides. Numerous deep permanent wrinkles across back (perpendicular to head-to-tail direction). |
| Skin sagging | |
| 0 | Numerous fine striations covering back and sides of body. Fine features run length of body (head-to-tail direction). Skin has pale purple-pink coloration. |
| 0.5 | Slight reduction in fine striations on back. Numerous fine features along sides run length of body (head-to-tail direction). Slight spotty blanching of skin on back. |
| 1.0 | Moderate reduction in fine striations on back and along sides. Slight blanching on skin on entire back. |
| 1.5 | Most fine striations gone. Slight nodular wrinkling on back, with no orientation to nodules. Moderate blanching of skin on entire back. |
| 2.0 | All fine striations gone. Moderate nodular wrinkling on back with no orientation to nodules. Complete blanching of skin on entire back. Slight loose folds of skin (head-to-tail direction) on sides. |
| 2.5 | All fine striations gone. Moderate to severe nodular wrinkling on back, with no orientation to nodules. Complete blanching of skin on entire back. Moderate loose folds of skin (head-to-tail direction) on sides. |
| 3.0 | All fine striations gone. Severe nodular wrinkling on back, with no orientation to nodules. Complete blanching of skin on entire back. Large loose folds of skin (head-to-tail direction) on sides. |

*The first appearance of tumors is usually at a grade of 1.5. Higher grades are almost always accompanied by tumors.

At 10 and 15 weeks, skin biopsies were performed on representative animals and were subjected to histologic evaluation using Hematoxylin, Eosin, and elastin stain.

Observation of the treated mice demonstrated a photoprotective effect of DHEA-treated mice in whom diminished erythema and diminished tumors were observed. Retinoid-treated mice developed an erythematous dermatitis. DHEA and DHEA-retinoid combination-treated mice developed less dermatitis. The combination DHEA and retinoic acid resulted in mice with the least evidence of photo-aging. The combination of DHEA 10 μg and retinoic acid 1 μg was the most effective in protecting against photo-aging. This combination also resulted in minimal erythema and had the lowest wrinkle index.

EXAMPLE 3

Preparation of a Phospholipid-DHEA-Retinoid Emulsion for Ophthalmic or Dermatologic Use A DHEA-lipid emulsion was prepared by adding about 500 mg crystalline DHEA and 50 mg crystalline retinoic acid (Sigma, Catalog No. R-2625) to a mixture of about 0.7 ml n-octanoic acid (Sigma, Catalog No. C2875). The mixture was heated to about 55° C. and stirred until the crystals were dissolved, about 10 min.

In a separate container, about 350 mg phosphatidylinositol (Sigma, Catalog No. P5766) and 350 mg phosphatidylglycerol (Sigma, Catalog No. P9524) were added to about 100 ml borate-buffered physiological saline, pH 7.2. Polyquaternium-1 (POLYQUAD, supplied by Alcon Labs., Inc., of Fort Worth, Tex.) was added to a final concentration of about 0.001% to inhibit bacterial growth in the emulsion. The mixture was heated to about 55° C. and stirred to facilitate the dispersion of the phospholipids, phosphatidylinositol, and phosphatidylglycerol in the saline.

The DHEA-retinoid-octanoic acid mixture, at 55° C., was slowly added to the phospholipid mixture with constant stirring. The mixture was stirred for about 30 min., to form a stable emulsion. The emulsion was then cooled to about 24° C., and about 0.1 ml alphatocopherol acetate (Sigma, Catalog No. T3001) was added with further stirring. The emulsion was transferred to sterile containers prior to use as eyedrops or to application to the skin.

EXAMPLE 4

A glossy, white cream containing DHEA and retinoic acid was prepared as follows (all quantities are wt/wt):

| Part | Components | g/100 g |
| --- | --- | --- |
| A | cetyl alcohol (CO-1695, Proctor and Gamble Co.), | 10.00 |
|   | Brij 721 | 4.00 |
| B | DHEA alcohol, | 0.75 |
|   | retinoic acid | 0.07 |
| C | water (deionized), | 79.93 |
|   | propylene glycol, | 5.00 |
|   | EDTA | 0.05 |
| D | sodium hydroxide (10% aqueous) | 0.10 |
| E | vitamin-E alcohol | 0.10 |

Part A was heated to 60° C., and Part C to 70° C. Part B was added to Part A and mixed until the crystals dissolved. Part C was slowly added to Parts A and B and agitated with an anchor-type stirring blade. Part D was then added, and the mixture was allowed to cool. Water was added to replace that which was lost due to evaporation, and, while the mixture was maintained, the ABCD mixture was cooled to 30° C. Part E was added after the ABCD mixture was cooled to below 30° C. The pH was adjusted to 5.5, if necessary, and the mixture was homogenized. The composition is applied to the skin at night.

EXAMPLE 5

Preparation of a DHEA-Retinoid Cream for Topical Treatment of a Mammal

A cream is prepared by the procedure described in Example 4, with the exception that the concentration of DHEA is reduced to 0.25%, retinoic acid is reduced to 0.01%, and 1.5% titanium dioxide is added to Part C. The resulting cream is applied to the skin during the day.

EXAMPLE 6

Preparation of a DHEA-Retinoid Composition for Intranasal Administration

A solution of hydroxypropyl-δ-cyclodextrin is first prepared by forming a saturated solution of 40 mg of hydroxypropyl-δ-cyclodextrin in 100 cc of water. The solution is decanted and undissolved cyclodextrin discarded. A second solution is made by dissolving 1000 mg of DHEA alcohol and 50 mg of retinoic acid in a minimum sufficient volume of ethanol to dissolve the crystals. The DHEA-retinoic acid, dissolved in ethanol, is added dropwise to the cyclodextrin solution, with constant mixing, at 30° C. Lyophilization, to remove 10% of the volume of the combined solution, is performed to remove most of the ethanol. The resulting DHEA-retinoid-hydroxypropyl-δ-cyclodextrin solution is administered nasally or orally by aerosolization.

EXAMPLE 7

Preparation of a DHEA Tablets for Sublingual and Oral Use

A solution of DHEA dissolved in gamma-cyclodextrin is prepared by the method described in Example 6. The sample is lyophilized to dryness, resulting in a white crystalline powder of the mixture of DHEA, retinoid, and cyclodextrin. The mixture is compressed into tablets for sublingual use. The tablets are dissolved under the tongue 3 times daily, to deliver up to 300 mg of DHEA and 15 mg of retinoic acid per day.

EXAMPLE 8

Preparation of a DHEA-Retinoid Combination for Oral Administration to a Mammal

Tablets are prepared by the procedure described in Example 7. The equivalent of 100 mg of DHEA and 5 mg of retinoic acid is administered orally 3 times a day.

EXAMPLE 9

Preparation of a DHEA-Retinoid Combination for Intravenous Administration to a Mammal A solution of DHEA, retinoic acid, and hydroxypropyl-δ-cyclodextrin is prepared by the procedure described in Example 6. The solution is filtered through a 0.2-micron filter, at 30° C. The resulting sterile filtrate is administered intravenously, using standard techniques, to deliver 50 mg of DHEA and 2.5 mg retinoic acid, 3 times a day, to an adult, and 2 mg/kg DHEA and 0.01 mg/kg retinoic acid to infants and children.

EXAMPLE 10

Additional DHEA-Retinoid Preparation for Intravenous Administration to a Mammal

Twenty mg of retinoic acid and 1000 mg of DHEA are dissolved in 1 cc of ethanol. This solution is added dropwise to a solution of 500 cc of 5% albumin and 500 cc of dextran, with constant mixing. 100% nitrogen is bubbled for 6 hrs. through the resulting suspension, with constant mixing. The suspension is aerated for 6 hrs. with 100% nitrogen, to drive off residual ethyl alcohol. The suspension is then filtered through a 0.2-micron filter using sterile techniques. Ten cc of this solution is administered intravenously 3 times daily to an infant, or, for an adult, 100 cc is administered intravenously 3 times daily.

The above description of exemplary embodiments of methods for treating epithelial disorders using combinations of DHEA and retinoids are for illustrative purposes. Variations will be apparent to those skilled in the art; therefore, the present invention is not intended to be limited to the particular embodiments described above. Also, the invention disclosed may be practiced in the absence of any element which is not specifically disclosed in the specification. The scope of the invention is defined in the following claims.

What is claimed is:

1. A composition for the treatment of epithelial damage in a mammal comprising a pharmacologically active retinoid and pharmacologically active DHEA wherein the combination is effective in preventing or reversing damage to the epithelium due to environmental oxidative agents and wherein the proportion of retinoid and DHEA is sufficient to overcome the undesirable side effects of each composition when used alone.

2. A composition as recited in claim 1 wherein the retinoid is selected from the group consisting of retinoic acid, 13-cis-retinoic acid, N-(4-hydroxyphenyl)retinamide, all-trans-retinoic acid, retinal palmitate, β-carotene, other precursors and derivatives of retinoic acid, vitamin A and vitamin A derivatives, and mixtures thereof.

3. A composition as recited in claim 1 wherein the DHEA is selected from the group consisting of the free alcohol of DHEA, DHEA-S, DHEA derivatives which retain the pharmacological activity of DHEA, and mixtures thereof.

4. A composition as recited in claim 1 wherein the retinoid is present at a concentration of about 0.01% to about 0.5%.

5. A composition as recited in claim 1 wherein the DHEA is present at a concentration of about 0.1% to about 1%.

6. A composition as recited in claim 1 wherein the composition is suitable for oral administration.

7. A composition as recited in claim 6 wherein the composition further comprises hydroxypropyl-δ-cyclodextrins.

8. A composition as recited in claim 1 wherein composition is suitable for intranasal administration.

9. A composition as recited in claim 8 wherein the composition further comprises cyclodextrins.

10. A composition as recited in claim 8 wherein the composition comprises about 1% of DHEA, about 0.05% of retinoic acid, and about 0.4% of hydroxypropyl-δ-cyclodextrin.

11. A composition as recited in claim 1 wherein the composition is suitable for topical administration.

12. A composition as recited in claim 11 wherein the composition further comprises additives selected from the group consisting of vitamin A, vitamin D, vitamin C., antioxidant peptides, ubiquinone, nucleotides, phospholipids, sphingolipids, macrophage stimulators, growth factors, immunomodulators, hormones, ultraviolet-light blockers, carriers, and mixtures thereof.

13. A composition as recited in claim 12 wherein the composition comprises about 0.75% DHEA, about 0.1% retinoic acid, and about 2% titanium dioxide in a cream base.

14. A composition as recited in claim 1 wherein the composition is suitable for intravenous administration.

15. A composition as claimed in claim 14 wherein the composition further comprises serum albumin and dextran.

16. A composition as recited in claim 14 wherein the composition comprises about 0.1% DHEA, about 0.05% retinoic acid, and about 5% serum albumin.

17. A composition as recited in claim 1 wherein the composition is suitable for sublingual administration.

18. A composition as recited in claim 17 wherein the composition further comprises a carrier such as hydroxypropyl cyclodextrin derivatives.

19. A composition as recited in claim 17 wherein the composition comprises about 1% DHEA, about 0.05% retinoic acid, and about 0.04% hydroxypropyl-δ-cyclodextrins.

20. A composition as recited in claim 1 wherein the composition is suitable for administration in the form of eyedrops.

21. A composition as recited in claim 20 wherein the composition further comprises phospholipids.

22. A composition as recited in claim 1 wherein the epithelial damage is selected from the group consisting of disorders of the skin, oral epithelium and disorders of the bladder epithelium.

23. A method for treating epithelial damage in a mammal comprising administering a pharmacologically active retinoid in an amount sufficient to counteract undesirable side effects of administered DHEA and a pharmacologically active DHEA in an amount sufficient to counteract undesirable side effects of administered retinoid to the mammal wherein the combination is effective in preventing or reversing damage to the epithelium due to environmental oxidative agents.

24. A method as recited in claim 23 wherein the treatment is administered topically.

25. A method as recited in claim 24 wherein the retinoid is administered in a dose of about 0.1%, three times daily, and the DHEA is administered in a dose of about 1%, three times daily.

26. A method as recited in claim 23 wherein the treatment is administered intravenously.

27. A method as recited in claim 26 wherein the retinoid is administered in a dose of about 1 mg, three times daily, and the DHEA is administered in a dose of about 30 mg, three times daily.

28. A method as recited in claim 23 wherein the treatment is administered orally.

29. A method as recited in claim 28 wherein the retinoid is administered in a dose of about 20 mg, three times daily, and the DHEA is administered in a dose of about 150 mg, three times daily.

30. A method as recited in claim 23 wherein the treatment is administered sublingually.

31. A method as recited in claim 30 wherein the retinoid is administered in a dose of about 20 mg, three times daily, and the DHEA is administered in a dose of about 150 mg, three times daily.

32. A method as recited in claim 23 wherein the treatment is administered intranasally.

33. A method as recited in claim 32 wherein the retinoid is administered in a dose of about 10 mg, three times daily, and the DHEA is administered in a dose of about 100 mg, three times daily.

34. A method as recited in claim 23 wherein the treatment is administered in the form of eye drops.

35. A method as recited in claim 23 wherein the epithelial damage is selected from the group consisting of disorders of the skin, oral epithelium and disorders of the bladder epithelium.

36. A method as recited in claim 23 wherein the retinoid is selected from the group consisting of retinoic acid, 13-cis-retinoic acid, N-(4-hydroxy-phenyl)retinamide, all-trans-retinoic acid, retinal palmitate, β-carotene, other precursors and derivatives of retinoic acid, vitamin A and vitamin A derivatives, and mixtures thereof.

37. A composition for the treatment of inadequate surfactant production in the lungs of a mammal comprising a pharmacologically active retinoid and a pharmacologically active DHEA.

38. A composition as recited in claim 37 wherein the retinoid is selected from the group consisting of retinoic acid, 13-cis-retinoic acid, all-trans-retinoic acid, retinal palmitate, β-carotene and other precursors of retinoic acid, vitamin A and vitamin A derivatives, and mixtures thereof.

39. A composition as recited in claim 37 wherein the DHEA is selected from the group consisting of the free alcohol of DHEA, DHEA-S, DHEA derivatives which retain the pharmacological activity of DHEA, and mixtures thereof.

40. A composition as recited in claim 37 wherein the retinoid is present at a concentration of about 0.01% to about 0.5%.

41. A composition as recited in claim 37 wherein the DHEA is present at a concentration of about 0.1% to about 1%.

42. A composition as recited in claim 37 wherein the composition is suitable for oral administration.

43. A composition as recited in claim 42 wherein the composition further comprises cyclodextrin derivatives.

44. A composition as recited in claim 42 wherein the composition is suitable for intravenous administration.

45. A composition as recited in claim 44 wherein the composition further comprises about 5% serum albumin.

46. A composition as recited in claim 45 wherein the composition further comprises liposomes.

47. A composition as recited in claim 45 wherein the composition further comprises cyclodextrin derivatives.

48. A method for treating inadequate surfactant production in the lungs of a mammal comprising administering a pharmacologically active retinoid and pharmacologically active DHEA.

49. A method as recited in claim 48 wherein the treatment is administered intravenously.

50. A method as recited in claim 49 wherein the retinoid is administered in a dose of about 0.01 mg/kg, three times daily, and the DHEA is administered in a dose of about 2 mg/kg, three times daily.

51. A method as recited in claim 48 wherein the treatment is administered orally.

52. A method as recited in claim 51 wherein the retinoid is administered in a dose of about 1 mg, three times daily, and the DHEA is administered in a dose of about 150 mg, three times daily.

53. A method for counteracting the toxicity of retinoid administration comprising administering a pharmacologically active DHEA to a patient to whom a retinoid is administered as a mode of treatment, wherein the DHEA is administered in an amount sufficient to counteract the toxic effects of the administered retinoid.

54. A method as recited in claim 53 wherein the DHEA is selected from the group consisting of the free alcohol of DHEA, DHEA-S, DHEA derivatives which retain the pharmacological activity of DHEA, and mixtures thereof.

55. A method as recited in claim 53 wherein the retinoid is selected from the group consisting of retinoic acid, 13-cis-retinoic acid, N-(4-hydroxy-phenyl) retinamide, all-trans-retinoic acid, retinal palmitate, $\beta$-carotene, other precursors and derivatives of retinoic acid, vitamin A and vitamin A derivatives, and mixtures thereof.

56. A method as recited in claim 53 wherein the mode of administering the pharmacologically active DHEA is selected from the group consisting of topical, intravenous, oral, sublingual, intranasal and by eye drops.

57. A method as recited in claim 53 wherein the DHEA is administered in a dose of about 30 mg to about 500 mg per day.

\* \* \* \* \*